United States Patent [19]

Stevens et al.

[11] Patent Number: 4,891,214

[45] Date of Patent: Jan. 2, 1990

[54] PARTICULATE EMULSIFIABLE HAIR CONDITIONING COMPOSITION

[75] Inventors: Frank H. Stevens, Columbus; Sheila E. Vetter, Powell, both of Ohio

[73] Assignee: Sherex Chemical Company, Inc., Dublin, Ohio

[21] Appl. No.: 251,228

[22] PCT Filed: Oct. 23, 1986

[86] PCT No.: PCT/US86/02236

§ 371 Date: Aug. 22, 1988

§ 102(e) Date: Aug. 22, 1988

[87] PCT Pub. No.: WO88/03016

PCT Pub. Date: May 5, 1988

[51] Int. Cl.$^4$ .................... A61K 7/08; A61K 7/06
[52] U.S. Cl. .................... 424/70; 424/401
[58] Field of Search .................... 424/70, 401, 69; 252/544, 547

[56] References Cited

U.S. PATENT DOCUMENTS

| 3,211,646 | 10/1965 | Berger | 252/8.8 |
| 3,803,137 | 4/1974 | Egan et al. | 564/291 |
| 4,098,822 | 7/1978 | Egan et al. | 252/88 X |
| 4,220,581 | 9/1980 | Cooperman et al. | 424/70 X |
| 4,275,055 | 6/1981 | Nachtigal et al. | 424/70 |
| 4,348,292 | 9/1982 | Ginn | 252/90 |
| 4,370,272 | 1/1983 | Wechsler et al. | 260/404 |
| 4,443,362 | 4/1984 | Guth et al. | 252/545 |
| 4,526,781 | 7/1985 | Goldberg et al. | 424/70 |
| 4,537,762 | 8/1985 | Fogel et al. | 424/70 |

FOREIGN PATENT DOCUMENTS

| 155806 | 9/1985 | European Pat. Off. . |
| 166232 | 1/1986 | European Pat. Off. . |
| 2224508 | 1/1974 | Fed. Rep. of Germany . |
| 2160421 | 12/1985 | United Kingdom . |

OTHER PUBLICATIONS

Muzyczko et al., 45, J. Am. Oil Chem. Soc., 720–725 (Nov. 1968).
Schoenberg et al., 94, Cosmetics & Toiletries, 57–60, 63, 64 (Mar. 1979).
McCarthy et al., 94, Cosmetics & Toiletries, 90–93 (Apr. 1979).

Primary Examiner—Ellis P. Robinson
Assistant Examiner—Susan S. Rucker
Attorney, Agent, or Firm—Scully, Scott, Murphy & Presser

[57] ABSTRACT

The addition of up to 80 percent by weight of a fatty alcohol, and up to 10 percent by weight of a fatty alkylamido alkyldialkylamine to a quaternary ammonium compound, results in a particulate composition which, when stirred into warmed, slightly acidified water, almost immediately forms an emulsion. The emulsion thus produced overcomes many problems usually associated with the formulation of emulsions, and is suitable for use as a hair conditioner.

9 Claims, No Drawings

PARTICULATE EMULSIFIABLE HAIR CONDITIONING COMPOSITION

BACKGROUND OF INVENTION

1. Field of Invention

This invention relates to particulate compositions which readily form hair conditioning emulsions, when stirred into heated, acidified water.

2. Description of the Related Art

Modern hair cleansing agents, especially shampoos, while efficiently removing soil from the hair and scalp, simultaneously remove natural protective oils. Repeated use of shampoos (e.g. on a daily basis, not an uncommon practice in our society) may not allow sufficient time for the body to replenish these protective natural oils. As a result, the hair becomes dry, brittle, loses its natural sheen, builds up static electric charges and is difficult to coif.

In order to overcome the deleterious effects of repeated hair washings and permit hair to be clean, yet at the same time attractive, the art has developed a spectrum of post-washing hair conditioning preparations.

Post-washing hair conditioning products well known to the art include cream rinses, spray conditioners, and setting lotions. It is also well known to the art that quaternary ammonium compounds are effective ingredients in such hair conditioning preparations. They are believed to be effective because they possess a positive electrostatic charge, which is attracted to and neutralizes the negative charges of hair protein. The mutual attraction of opposite electrostatic charges thus causes the quaternary ammonium compound to tend to remain on the hair. This tendency to remain on the hair is termed substantivity. Substantive quaternary ammonium compounds not only neutralize the electrostatic charges of hair, but also may provide lubricity, by virtue of their long chain, (i.e. fatty) substituents.

Phenomena associated with quternary ammonium compounds in hair conditioning preparations are discussed for example in an article by T. G. Schoenberg "Role of Alkyl Amino Amine Salts in the Modern Hair Conditioner", *Cosmetics and Toiletries,* Volume 94, pages 57 et al (1979), which also includes detailed instructions for the preparation of hair care formulations. Hair care formulations prepared with lanolin fatty acid quaternary ammonium compounds are described in "Effects of the Use of Lanolin Acid Quaternary in Human Hair Conditioning Preparations" by J. R. McCarthy and J. M. Laryea, *Cosmetics and Toiletries,* Volume 94, pages 90 et al, (1979). U.S. Pat. No. 4,526,781 teaches the use of betaines in hair care formulations. Betaines are quaternary ammonium compounds characterized by a zwitterionic structure and exemplified by the reaction product of sodium chloracetate with a fatty dimethyl tertiary amine. The use of quaternary ammonium compounds derived from halo-esters of fatty alcohols as hair conditioners is taught by U.S. Pat. No. 4,370,272. The preparation of a mixture of quaternary ammonium compounds suitable for use in rinsing compositions for human hair is described in U.S. Pat. No. 3,803,137. U.S. Pat. No. 3,211,646 teaches the antistatic properties of mixtures of fatty acid dimethylaminopropyl amides with quaternary ammonium compounds derived from said dimethylaminopropyl amides.

Quaternary ammonium compounds are marketed to formulators as solutions, dispersions, and aqueous pastes. These materialsrequire bulky storage and handling facilities. They are more costly to ship than the solvent-free quaternary ammonium compound, and present formulation difficulties. Solutions and dispersions tend to lose solvent, thus changing the concentration of quaternary ammonium compound dispensed. Sufficient loss of solvent or water may result in precipitation of the quaternary compound itself, leading to unequal distribution. Pastes are physically difficult to dispense and suffer from the same loss of solvent problems as solutions and dispersions. In addition, pastes and dispersions tend to be difficult to emulsify. Quaternary ammonium compounds may be obtained as solids by evaporatively removing the solvents; however, in their solid form, quaternary ammonium compounds are even more difficult to disperse and emulsify than pastes or dispersions. The use of solid quaternary ammonium compounds may introduce variables into the formulation of hair care products because of the presence of variable quantities of residual water or solvents.

In addition to quaternary ammonium compounds, post-washing hair care formulations known in the art may include fatty alcohols and fatty alkylamido alkyldimethylamines, among others. Preparation, physical characteristics and application in cosmetic chemistry of fatty amidoamine derivatives are described in an article by Muzyczko, et. al. (T. N. Muzyczko et. al. "Fatty Amidoamine Derivatives: N,N,-Dimethyl-N-(3 alkylamidopropyl) amines and their Salts." J.O.A.C.S., 45 Pg. 720–5 (1968). They may be prepared by reacting fatty acids with dialkyl amines. The fatty acids may be derived from naturally occuring fats and oils, and thus would have a chain length distribution from about $C_8$ to about $C_{22}$. Synthetic fatty acids may also be used. The combination of fatty alkylamido dimethylamines and a fatty dialkylbenzylamonium chloride for use as a fabric softener is described in German Patent number 2,224,508. A liquid detergent concentrate system packaged for single use application as an industrial cleanser, including fatty alcohols and quaternary ammonium compounds, is taught by U.S. Pat. No. 4,348,292. Thus, the prepackaged liquid concentrate is admixed with the proper quantity of water to obtain a cleansing solution for hard surfaces, bathrooms, and floors. The liquid concentrate taught by said patent consists of two immiscible layers within the same container.

SUMMARY OF THE INVENTION

We have discovered a particulate composition containing a quaternary ammonium compound, which may be used for the preparation of post-washing hair conditioning emulsions. Thus, the addition of the particulate composition of the present invention with stirring, to slightly acidified warm water, almost immediately produces an emulsion suitable for use as a post-washing hair conditioner. The problems usually associated with preparing formulations (e.g. incorporating aqueous pastes or dispersions of quaternary ammonium compounds along with other ingredients) are thereby eliminated.

A composition according to this invention may be obtained by melting together a quaternary ammonium compound, a fatty alcohol, and an alkylamido alkyldimethylamine, thoroughly mixing the molten materials, and then congealing the moltent mixture to form a particulate (e.g., by flaking). The particulate product thus obtained is a convenient means of incorporating a quaternary ammonium compound into a hair care emulsion without the drawbacks usually associated with the preparation of such emulsions.

DETAILED DESCRIPTION OF THE INVENTION

This invention relates to a particulate composition which when added to stirred, heated, acidified water essentially instantly produces a stable emulsion suitable for use as a post-washing hair conditioner. The quaternary ammonium compound contained in the composition of this invention is substantive to the hair. Quaternary ammonium compounds useful for the purposes of this invention may be produced by means well known to the art. It is well known in the art that tertiary amines may be quaternized by such agents as benzylchloride, methyl chloride, dimethyl sulfate, and sodium chloroacetate. Virtually all tertiary amines are amenable to quaternization, however, for the purposes of this invention at least one substituent of said tertiary amine should be a long chain, (i.e.(fatty) alkyl, alkoxyl or alkylamido) group. Such fatty alkyl substituents are preferably mixtures of chain lengths of branched and/or straight chain aliphatic moieties in the range of from about 10 to about 20 carbons. These may be obtained by using amines derived from natural sources such as tallow, where the predominant chain lengths are $C_{16}$ and $C_{18}$, or other naturally occuring fats or oils with aliphatic chain lengths varying from about $C_{10}$ to about $C_{20}$, as is well known in the art. Further, it is also well known in the art that methyl chloride may be reacted with secondary amines in a mole ratio of 2:1 to produce quaternary ammonium compounds use for hair conditioning. The quaternary ammonium compounds obtained by these methods and use for this invention are of general formula:

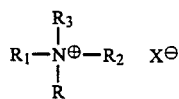

where R, $R_1$, $R_2$ and $R_3$ are $C_1$-$C_{20}$ branched or straight chain alkyl groups or mixtures thereof, and $X^-$ is the anionic residue of an alkylating agent. The preferred quaternary ammonium compounds of this invention may be prepared by the method taught by U.S. Pat. No. 3,803,137 by quaternization of a mixture of straight chain and branched chain amines as set forth in Example 1, below.

In order to obtain the composition of this invention an effective amount of said preferred quaternary ammonium compounds obtained as solids are melted together with fatty alcohols and alkylamido alkyldimethylamines. Fatty alcohols may be derived from either natural or synthetic sources, and may have chain lengths from $C_8$ to $C_{22}$ or mixtures thereof. The preferred fatty alcohol of this invention is a mixture of 65 parts stearyl alcohol with 35 parts of cetyl alcohol (Adol 63; Sherex Chemical Company, Dublin, Ohio). Alkylamido alkyldimethylamines derived from naturally occuring and synthetically produced fatty acids may be useful in this invention. Those derived from natural fats and oils have chain length distributions from about $C_8$ to about $C_{22}$. The preferred alkylamido akyldimethylamine is stearamido propyldimethylamine. The fatty alcohol functions as an emollient or lubricant, a combing aid and viscosity builder. The fatty alcohol, although not substantive to the hair, does coat it and provides some lubrication. The function of the alkylamido alkyldimethylamine is to provide both emulsion stabilization and hair conditioning properties. The ingredients of the composition of this invention may be added to each other in any order. Thus, the preferred composition of this invention may be prepared by melting together 74 parts of the said preferred fatty alcohol with 20 parts of the said preferred quaternary ammonium compound and 5.8 parts of the said preferred alkylamido alkyldimethylamine, at about 80° C. The mixture was stirred until uniform, and cooled to approximately 50° C., to obtain a friable solid. Cooling may, of course, be accomplished on a chiller roll, chill belt or like device, whereby a particulate in the form of flakes may be obtained, as is well known in the art. The quaternary ammonium compound, or mixtures thereof, should melt above approximately 30° C., and the fatty alcohol or mixture of fatty alcohols should melt above about 50° C., in order to obtain a friable solid. In order to obtain a stable hair conditioning emulsion, 8 parts of the particulate of this invention were admixed with water at approximately 70° C., to which sufficient citric acid had been added to adjust the pH to approximately 4.5. Upon stirring, a stable emulsion, suitable for use as a post-washing hair conditioner, was, almost immediately, obtained. None of the difficulties inherent in the use of quaternary ammonium compounds as pastes or dispersions, or the problems associated with the preparation of emulsions were encountered. Optional ingredients, e.g. perfume, coloring, may then be added to obtain a formulated product.

To further illustrate the efficacy of this invention the following non-limiting examples are set forth.

EXAMPLE 1

A mixture of quaternary compounds derived from a mixture of fatty alcohols was prepared according to the process set forth in U.S. Pat. No. 4,098,822. Thus, a mixture of fatty alcohols, consisting of equal parts of C12-C15 primary alcohols containing 20-25% methyl branched isomers (Neodol 25; Shell Chemical Co.) and C16-C18 primary alcohols (Alfol 1618; Continental Oil Company), was charged to a reactor. Typical distribution for the alcohol mixture is set forth below; sc denoting straight chain, b denoting branch chain isomers respectively.

| isomer | weight % |
| --- | --- |
| C11 | 1.0 |
| C12 sc | 9.25 |
| C12 b | 3.10 |
| C13 sc | 9.40 |
| C13 b | 3.15 |
| C14 sc | 11.65 |
| C14 b | 3.55 |
| C15 sc | 7.35 |
| C15 b | 2.40 |
| C16 sc | 31.50 |
| C18 sc | 17.00 |
| C20 | 0.50 |

The alcohol mixture was sparged with a mixture of hydrogen and ammonia at 180°-190° C. in the presence of nickel catalyst, water and ammonia being continuously removed during the course of the reaction. When the total nitrogen content was found to remain constant, requiring approximately 6 hours, the sparge of gasses was stopped, and the reactor was cooled to approximately 100° C. Vacuum was applied to remove residual hydrogen, ammonia, and water. The reactor was then unsealed, and the product, predominantly di-fattyalkyl secondary amines filtered, to remove catalysts. Quaternization was accomplished by reacting of mole of said secondary amines dissolved in isopropanol with 2 moles of methyl chloride, in a sealed, agitated reactor in the presence of concentrated (73%) aqueous sodium hydroxide. The temperature within the reactor was maintained at 90°–95° C., and methyl chloride was continuously added, so as to maintain the pressure at about 3 atmospheres, until the free amine content was less than 1.5% by weight. The reaction mixture was then cooled to about 55° C., diluted with isopropanol, and filtered to remove byproduct sodium chloride. A mixture of quaternary ammonium chlorides, predominantly dialkyldimethyl, was isolated by vacuum removal of residual water and isopropanol had the formulae:

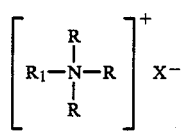   I

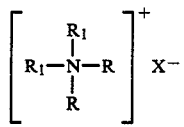   II

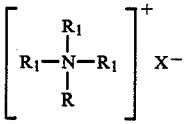   III wherein $R_1$ collectively represents the alkyl residue of a primary alcohol mixture composed of 30–70 wt. percent of (a) straight-chain $C_{16}$–$C_{22}$ alcohols and correspondingly from 70–30 wt. percent of (b) $C_8$–$C_{15}$ Oxo alcohols consisting essentially of a mixture of straight-chain and single methyl branched isomers, and (a) and (b) being in relative proportions so that from about 95–80 wt. percent of said $R_1$ groups are straight-chain alkyl and correspondingly from 5–20 wt. percent are said branched alkyl, R is a $C_1$–$C_3$ alkyl group, $X^-$ represents a chloride, bromide or iodide anion, and wherein said mixture of quaternaries is essentially composed of 0–10 wt. percent of compounds of Formula I, 60–85 wt. percent of compounds of Formula II, and 5–25 wt. percent of compounds of Formula III.

The isolated mixture of quaternaryammonium compounds was found to melt at about 30° C. by melting on a Fisher-Johns melting apparatus, (Fisher Scientific Co., Pittsburgh, PA).

EXAMPLE 2

Twenty parts of the product of Example 1 were admixed with 74.2 parts of a mixture consisting of (a) 65 parts of stearyl alcohol and 35 parts of cetyl alcohol (Adol 63; Sherex Chemical Company, Dublin, Ohio), and (b) 5.76 parts of stearamido propyldimethylamine. The molten mixture was stirred until uniform, then poured out onto a flat sheet and allowed to cool to approximately 25° C. The resulting solid was then easily broken up to obtain non-adhering flakes.

EXAMPLE 3

A hair conditioning emulsion was prepared by adding 8 parts of the particulate product of Example 2(DPSC 131-130-1) to 92 parts of water at 70°–80° C. which contained sufficient citric acid (approximately 0.5 parts) to bring the pH to between 4 and 5. Upon stirring, an emulsion formed almost immediately. This emulsion was stored at room temperature and appeared to be stable, i.e. did not separate with time.

EXAMPLE 4

A swatch of standard European human hair (Chicago Hair Goods, Chicago, Ill.) weighing 3.0 grams was washed with standard shampoo (i.e. a solution of sodium lauryl sulfate), and rinsed. To the wet washed swatch, 0.5 ml. of the product of Example 3 was applied, and worked into the hairswatch. The swatch was then rinsed with warm water (30°–40° C.), drip dried and set up on hair rollers. The rolled hair swatches were allowed to dry at ambient conditions (20° C., 50% relative humidity). When dry, the rollers were taken down and the swatches were combed out. When compared with swatches of standard hair which were not treated with the product of Example 3, noticeable differences were observed. The untreated hair did not comb evenly, supported a static charge, was coarse to the touch, brittle and appeared dull. The swatches treated with the product of Example 3, on the other hand, were glossy, combed easily, and did not support static charges.

EXAMPLE 5

The product of Example 2 (DPSC 131-130-1) was formulated into two different preparations which are each imitative of a commercially available post-washing hair care product. Thus, the procedure of Example 3 was followed to produce an emulsion to which additional ingredients were added. The respective formulations are set forth in the table below.

| Formulation | SC-179-170-I (Parts) | SC-179-170-II (Parts) |
| --- | --- | --- |
| DP SC 131-130-1 | 5.0 | 5.0 |
| Citric Acid | qs pH 4.5 | qs pH 4.5 |
| Germicide | 0.3 | 0.3 |
| Propylene Glycol | — | 0.3 |
| Silicone | — | 0.3 |
| Perfume | 0.1 | 0.1 |
| Water | 94.6 | 94.0 |

A blank, that is, a composition imitative of a post-washing hair care product, but containing no hair conditioning composition was formulated by mixing the ingredients set forth in the table below:

| Blank Formulation | SC 155-156 (parts) |
| --- | --- |
| Polyacrylic emulsifier | 0.3 |
| Polyethylene glycol with an average mol. wt. of 6000 | 0.1 |
| Perfume | 0.2 |
| NaOH | 0.12 |
| Water | 99.28 |

Formulation SC 179-170-I was evaluated against the blank (SC 155-156, and against a commercially available hair conditioning emulsion containing similar ingredients, designated as Control I. Formulation SC 179-170-II was evaluated against a commercially available hair conditioning emulsion containing silicone, propylene glycol, and other similar ingredients, designated as Control II. Each formulation was blind coded so as to preclude bias by either cosmetologist or panelist. Evaluations were conducted on separate panels of eight volunteers each, randomly selected for age, sex, and hair type. Thus, the panelists had their hair shampooed and treated by a licensed, professional cosmetologist, under beauty salon conditions. Each test subject's hair was shampooed twice with the same commercially available non-conditioning shampoo. For the first washing, 3 ml. of shampoo was applied, lathered and thoroughly rinsed. The hair was again washed using 2 ml. of shampoo, and then thoroughly rinsed. The set hair was divided into right and left halves from forehead to the back of the neck. Four (4) ml. of a test hair care formulation was applied to one side of the head, and 4 ml. of either a control or blank formulation was applied to the other. The formulations were individually, manually washed into the hair carefully so as not to mix the two sides, and let stand for 2 minutes. Each side was individually rinsed for 10 seconds to determine rinsibility, i.e. ease of removal. Each half of the head was then thoroughly rinsed. A comb was passed through each side simultaneously to evaluate resistance and detangling. Combing was continued to evaluate wet combability. The hair was then dryed with a salon dryer and combed again to evaluate dry combability, and the other criteria set forth in the evaluation table below.

The fingers were run through the hair to evaluate "feel." The data tabulated below are evaluations by the professional cosmetologist who performed each salon test. Certain criteria were subjectively evaluated by each panelist. Each criterion was rated on a scale of 1 to 6, 6 being the best. The scores for each half of a head of hair were summed, then averaged. The data presented in Table I below are the percentage scores for each criterion, as evaluated by the professional cosmetologist. The definitions of the evaluation criteria follow the table.

TABLE I

Average Percentage Score in Salon Evaluation of Hair Conditioning Formulations (Cosmetologist's Evaluation)

|  | SC-179-170-I | Blank (SC155-156) | SC-179-170-I | Control I | SC-179-170-II | Control II |
|---|---|---|---|---|---|---|
| Rinsibility* | 74 | 26 | 36 | 64 | 60 | 31 |
| Detangling | 74 | 26 | 47 | 53 | 53 | 47 |
| Wet Comb | 77 | 23 | 59 | 41 | 58 | 42 |
| Dry Comb | 75 | 25 | 67 | 23 | 42 | 58 |
| Static | 67 | 33 | 42 | 58 | 68 | 32 |
| Feel | 82 | 18 | 65 | 35 | 50 | 50 |
| Manageability | 78 | 22 | 52 | 48 | 40 | 60 |
| Body | 81 | 19 | 57 | 43 | 66 | 34 |
| Shine | 79 | 21 | 45 | 58 | 59 | 41 |
| Curl Retention | 79 | 21 | 45 | 55 | 68 | 32 |

*Criteria are defined as:
Rinsibility: The ability of the product to rinse and leave the hair feeling clean yet conditioned.
Detangling: The products performance as an aid in reducing tangles in the hair.
Wet Comb: Resistance of hair to combing when wet.
Dry Comb: Same as Wet Comb but after the hair has been styled and dried.
Static: The relative reduction of static flyaway.
Feel: How soft and silky the product leaves the hair.
Manageability: How well the hair behaves when styled.
Body: The fullness of the hair after it is dry.
Shine: The comparative shine or sheen of the two products.
Curl Rentention: How well the hair holds its style over time.

The individual panelists also reported their subjective evaluations of certain of the criteria within 24 hours after salon evaluations. These scores were summed and the average values obtained are reported in Table II below.

TABLE II

Average Percentage Score in Salon Evaluation of Hair Conditioning Formulations (Panelist's Evaluation)

|  | SC-179-170-I | Blank (SC155-156) | SC-179-170-I | Control I | SC-179-170-II | Control II |
|---|---|---|---|---|---|---|
| Static | 50 | 50 | 48 | 52 | 53 | 47 |
| Feel | 45 | 55 | 51 | 49 | 53 | 47 |
| Dry Comb | 46 | 54 | 45 | 55 | 54 | 46 |
| Body | 45 | 55 | 55 | 45 | 52 | 48 |
| Shine | 53 | 47 | 51 | 49 | 56 | 44 |
| Curl Retention | 57 | 43 | 53 | 47 | 50 | 50 |

*Criteria defined as above.
**The time elapsed between salon treatment and panelist evaluations permitted the re-absorption of moisture and natural oils by the hair, resulting in little descrimination among the materials evaluated.

It is evident from the data on Tables I and II, above, that the post-washing hair care formulations obtained from the emulsifiable particulate composition of this invention are at least as effective as the commercially prepared hair care emulsions with which they were compared.

We claim:
1. A particulate emulsifiable hair conditioning composition comrising: (a) from 40–80% by weight of aliphatic alcohol of 8 or more carbons, or mixtures thereof; and (b) from 20–60% of a quaternary ammo- nium compound or mixtures thereof miscible with said alcohol mixture; and (c) from 2-10% of a fatty alkylamido alkyldialkylamine of the general formula

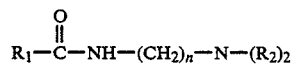

where;
n is 1-6
$R_1$ is C8 to C28 alkyl group,
$R_2$ is a C1 to C5 alkyl group;
such that said composition melts at or above 30° C.

2. The composition as in claim 1 where the aliphatic alcohol is a mixture of 50-80% stearyl alcohol with up to 50% cetyl alcohol.

3. The composition as in claim 2 where the aliphatic alcohol is a mixture of 65% stearyl alcohol and 35% cetyl alcohol.

4. The composition as in claim 2 where the quaternary ammonium compound is of the general formula:

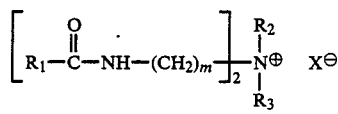

where:
$R_1$ is a $C_6$-$C_{22}$ alkyl group
$R_2$ is a $C_1$-$C_3$ alkyl group
$R_3$ is a $C_1$-$C_3$ alkyl group, a benzyl group, or a phenyl group
m is 1-6,
$X^-$ is the monovalent anionic residue of an alkylating agent.

5. The composition as in claim 2 where the quaternary ammonium compound is of general formula

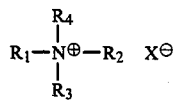

where:
$R_1$ and $R_2$ are $C_8$-$C_{18}$ alkyl groups,
$R_3$ is a $C_1$-$C_3$ alkyl group,
$R_4$ is a $C_1$-$C_3$ alkyl group, a phenyl group or a benzyl group,
$X^-$ is the monovalent cation residue from alkylating agent.

6. The composition as in claim 3 where the quaternary ammonium compound consists of a mixture of quaternary ammonium compounds having the formulae

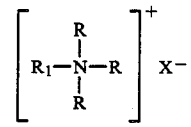

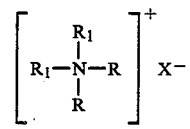

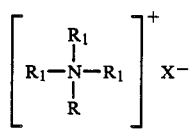

wherein $R_1$ collectively represents the alkyl residue of a primary alcohol mixture composed of 30-70 weight percent of (a) straight chain $C_{16}$-$C_{22}$ alcohols and correspondingly from 70-30 weight % of (b) $C_8$ to $C_{15}$ oxoalcohols consisting essentially of a mixture of straight chain and single methyl branched isomers, said (a) and (b) being in relative proportions so that from about 95-80 weight percent of said $R_1$ groups are straight chain alkyl and correspondingly from 5-20 weight percent are said branched alkyl, R is a $C_1$ to $C_3$ alkyl group, X represents a chloride, bromide, or iodide anion, and wherein said mixture of quaternaries is essentially composed of 0-10 weight percent of compounds of formula I, 60-85 weight percent of compounds of formula II, and 5-25 weight percent of compounds of formula III.

7. The composition as in claim 6 where X is chloride.

8. The composition as in claim 7 where the fatty alkylamido alkyldialkylamine is such that $R_1$ is predominantly a $C_{17}$ alkyl group, n is 3, and $R_2$ is a methyl group.

9. The composition as in claim 8 where the aliphatic alcohol mixture is present in 70-80% by weight, the quaternary ammonium compound is present in 10-30% by weight.

* * * * *